United States Patent [19]
Giese et al.

[11] Patent Number: 5,445,966
[45] Date of Patent: Aug. 29, 1995

[54] EXTRACTIVE HYDROGENATION FOR CHEMICAL ANALYSES

[75] Inventors: Roger W. Giese, Quincy; Mohammad S. Itani, Winthrop, both of Mass.

[73] Assignee: Northeastern University, Boston, Mass.

[21] Appl. No.: 49,278

[22] Filed: Apr. 20, 1993

[51] Int. Cl.⁶ ............................................. G01N 30/00
[52] U.S. Cl. ...................................... 436/159; 436/63; 436/86; 436/103; 436/71; 436/127; 436/161
[58] Field of Search ...................... 436/127, 63, 71, 66, 436/86, 103, 159, 161

[56] References Cited

PUBLICATIONS

D. Cooperberg, "Industrial Applications of Hydrogen" in Hydrogen: Its Technology and Implications, vol. IV, Utilization of Hydrogen (K. E. Cox, ed.), CRC Press, pp. 191–200 (1979).
Cooke et al., "Carbon Skeleton Capillary Gas Chromatography," J. Chrom. 193:437–443 (1980).
Schein et al., "Reduction of Pyrimidines," Meth. Enzymol. 12A:38–45 (1967).
Quinn et al., "The Role of Unsaturtated Lipids in Membrane Structure and Stability," Prog. Biophys. Mole. Biol. 53:71–103 (1989).
Swaminathan et al. "Reductive metabolism of the . . . "Biochem. Pharmacol, 29 (24) 1980 pp. 3285–3292.
Chiu et al. "Selective Catalytic Reduction of . . . " Steroids vol. 34 No. 3 pp. 361–364 Sep. 1979.
Streitweiser et al. Introduction to Organic Chemistry 1985 pp. 253–255 and p. 289.
Reusch, An Introduction to Organic Chemistry 1977 pp. 236–237.
Guido et al. "Quantitation of hydroperoxy-eicosatetraenoic . . . " Analytical Biochemistry 209, 123–129, Feb. 15, 1993.
Bakthavachalam et al. "Release of 2-aminofluorene . . . " Journal of Chromatography 538, 447–451, 1991.
Kresbach et al. "Apparatus for analytical hydrogenation . . . " Analytica Chimica Acta, 248, 615–618, 1991.
Harada et al. "Stereoselective Catalytic . . . " Bull. Chem. Soc. Jpn. 57, 1040–1045 1984 (vol. 57 No. 4).

Primary Examiner—James C. Housel
Assistant Examiner—Rachel Heather Freed
Attorney, Agent, or Firm—Weingarten, Schurgin, Gagnebin & Hayes

[57] ABSTRACT

A general purpose technique called extractive hydrogenation analysis, useful for both trace component and imaging analysis of samples containing organic matter. In processes according to the invention, organic matter is thoroughly decomposed in the presence of a hydrogenation catalyst under substantially aqueous conditions into products, and one or more of the products is then detected.

26 Claims, 18 Drawing Sheets

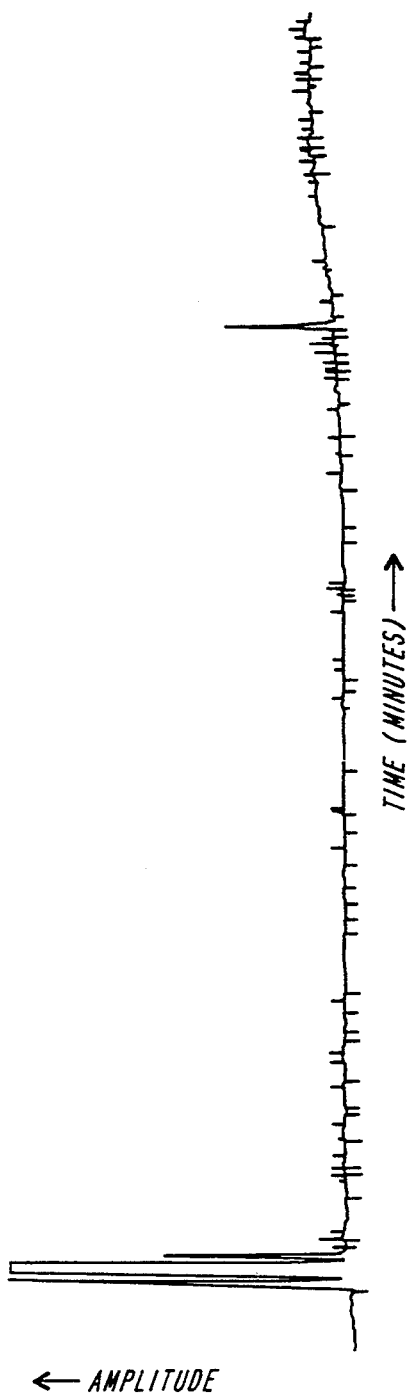

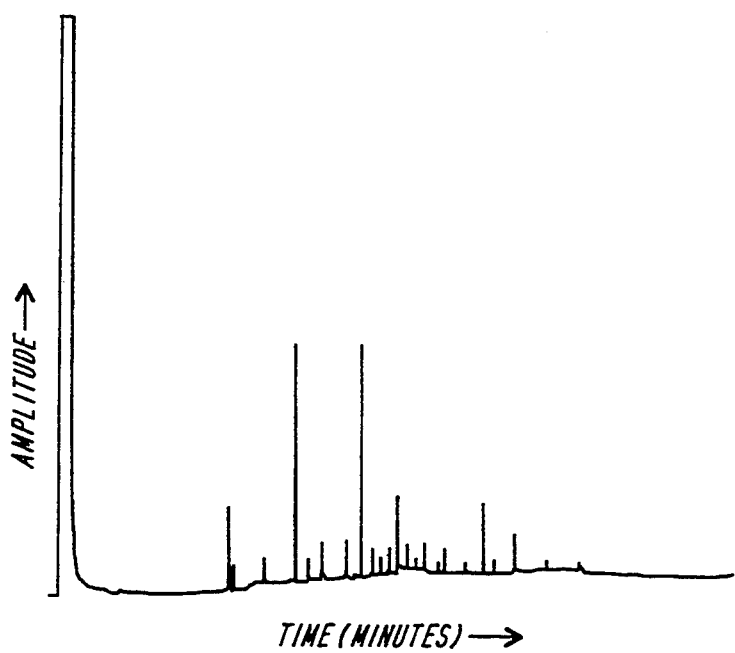
FIG. 7A
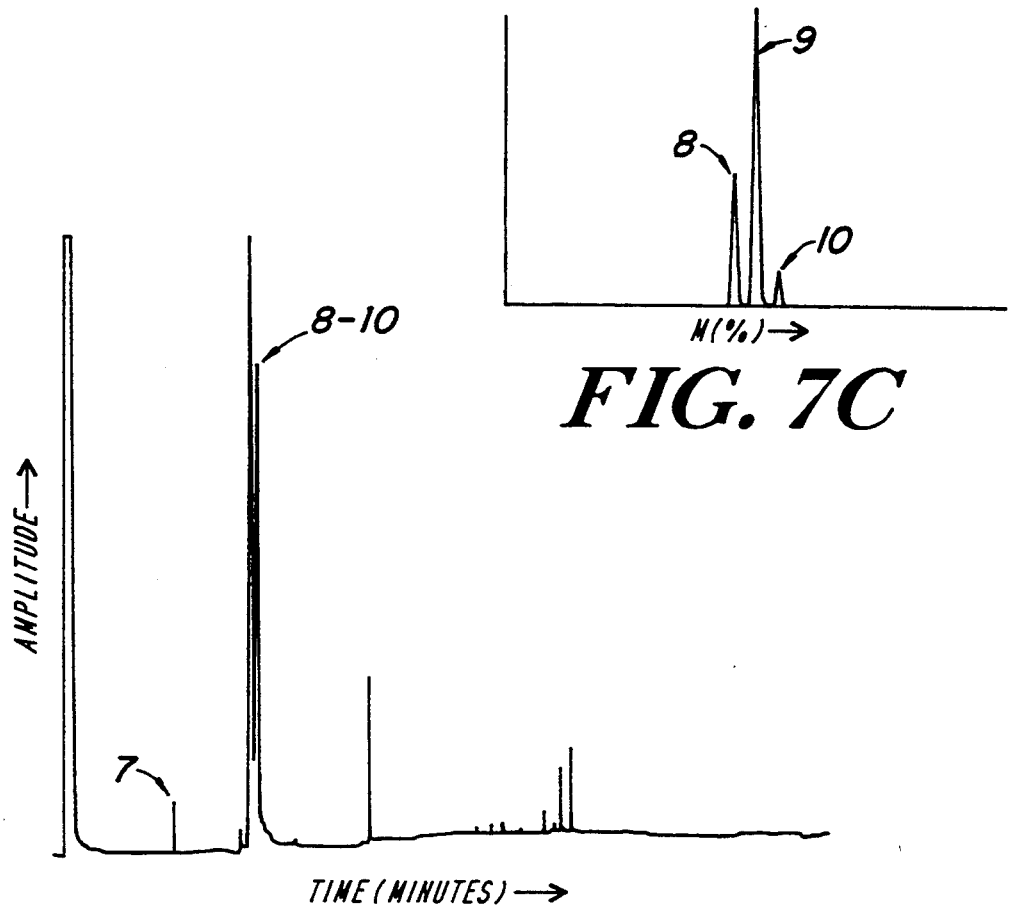
FIG. 7C
FIG. 7B

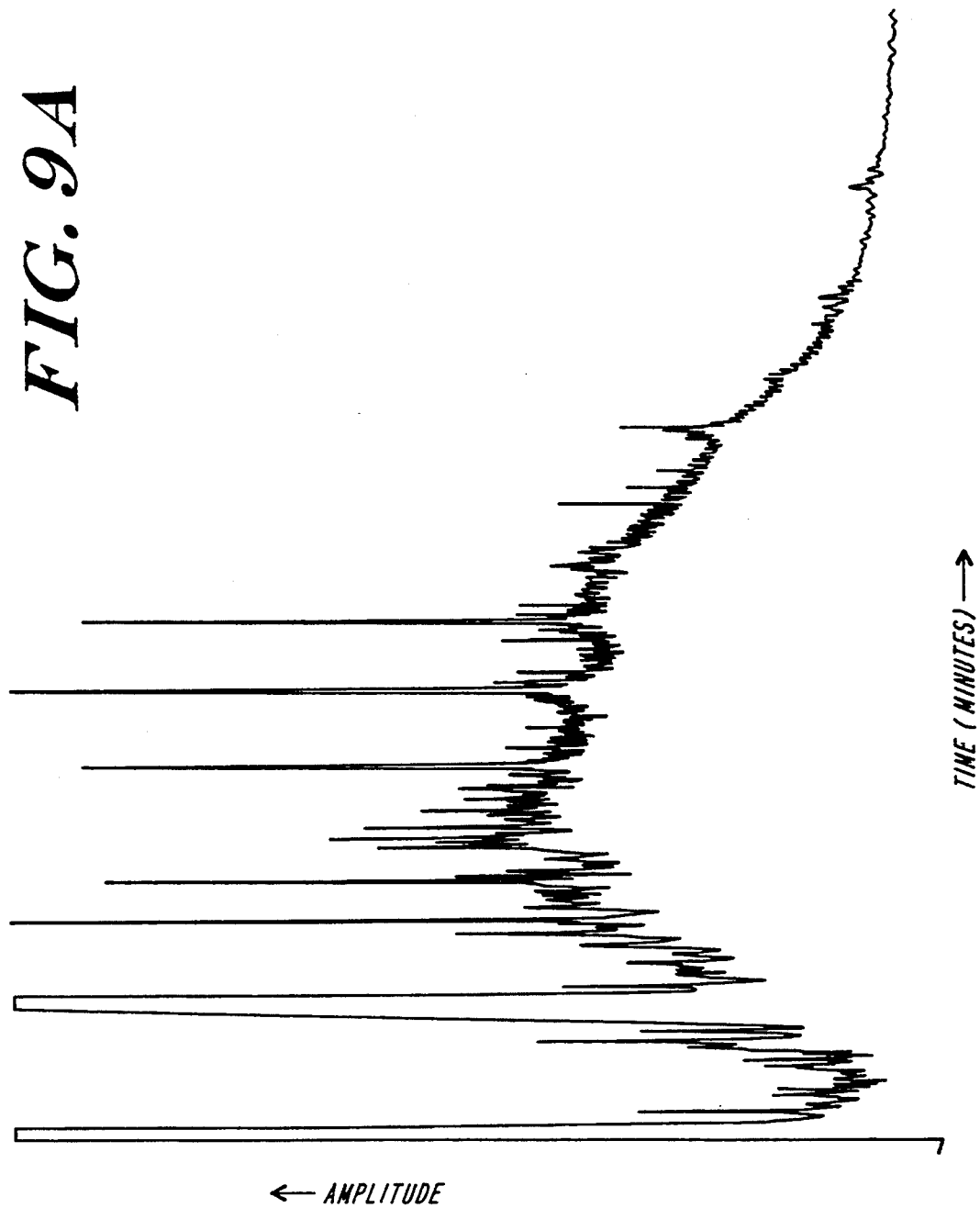

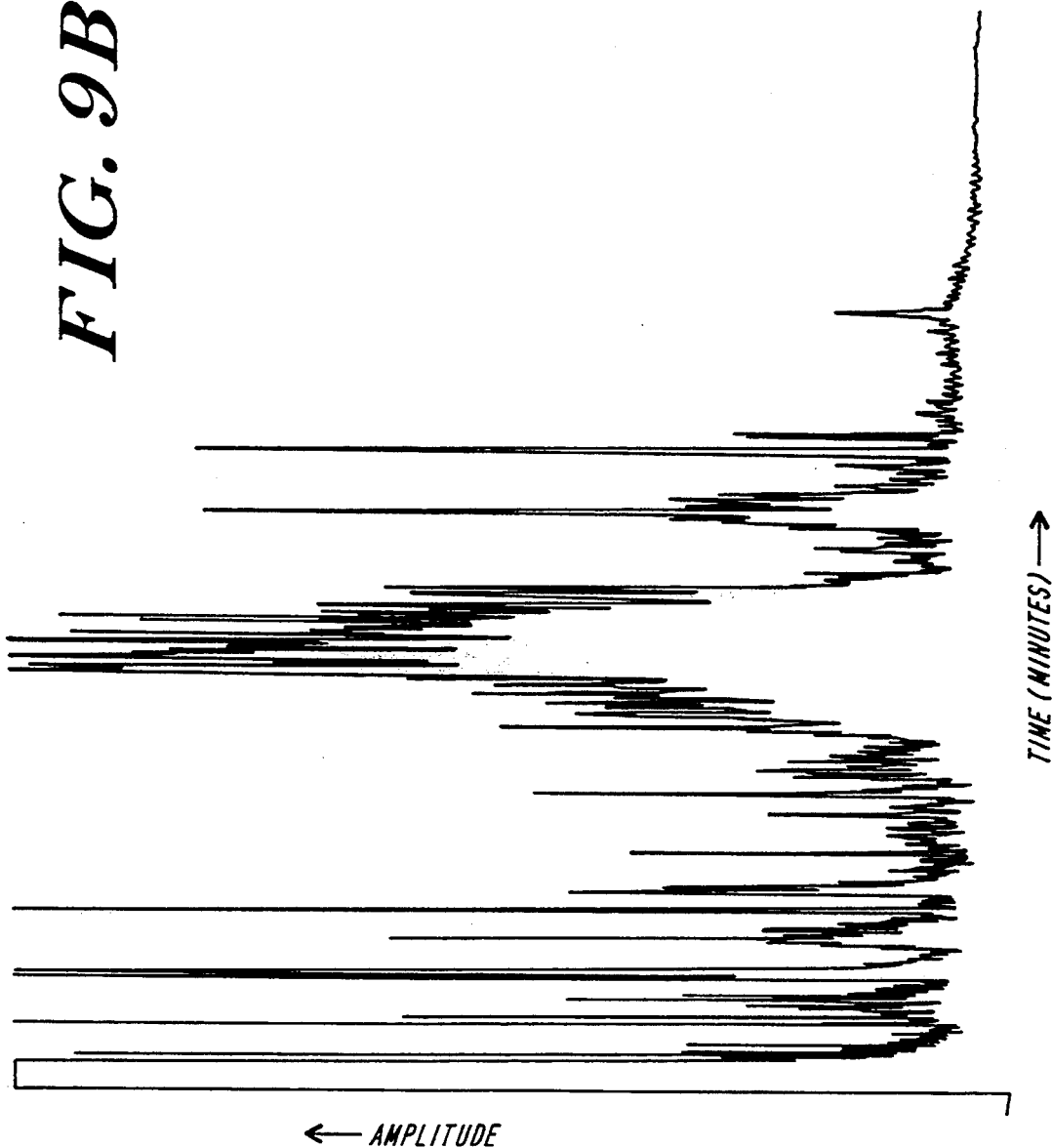

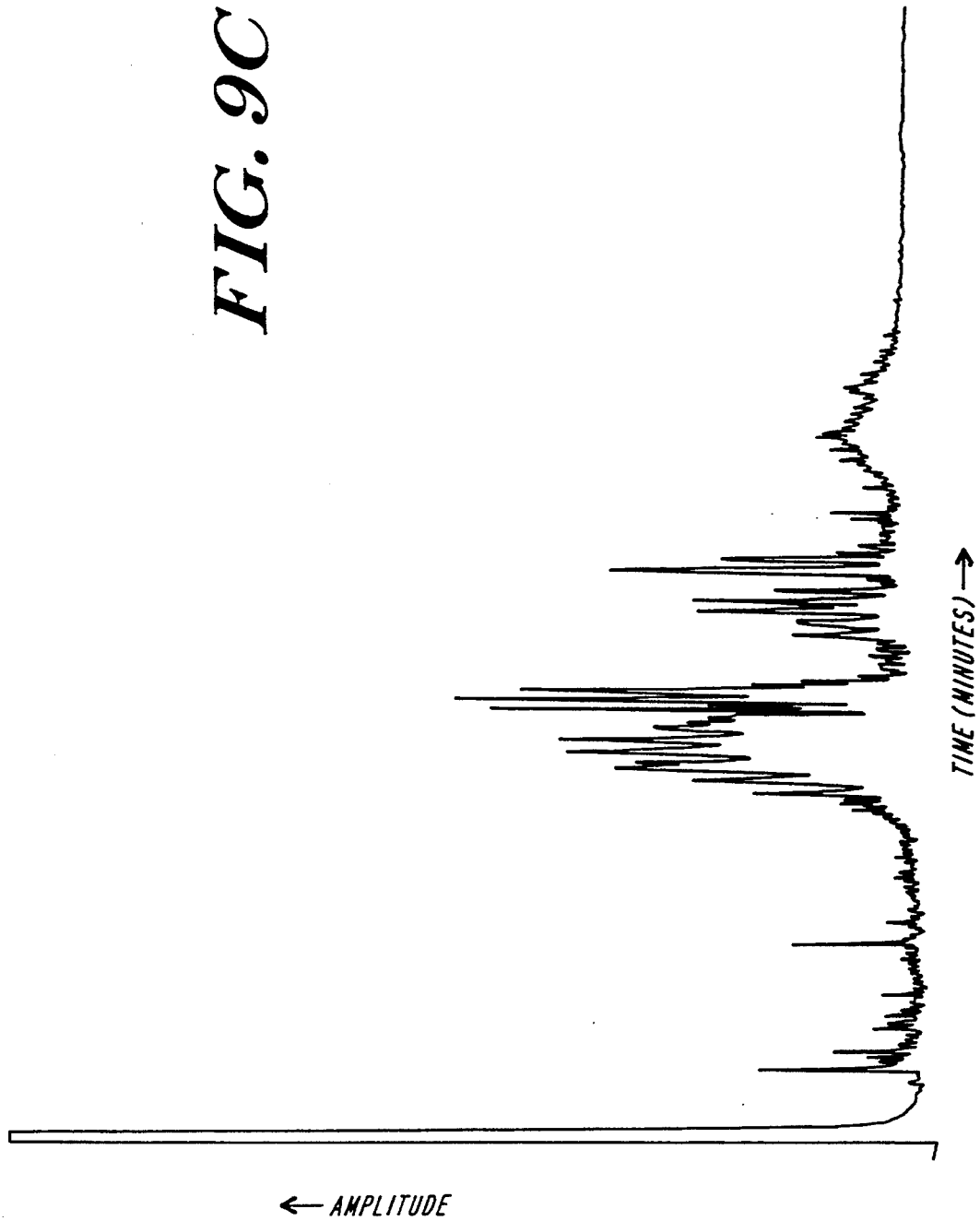

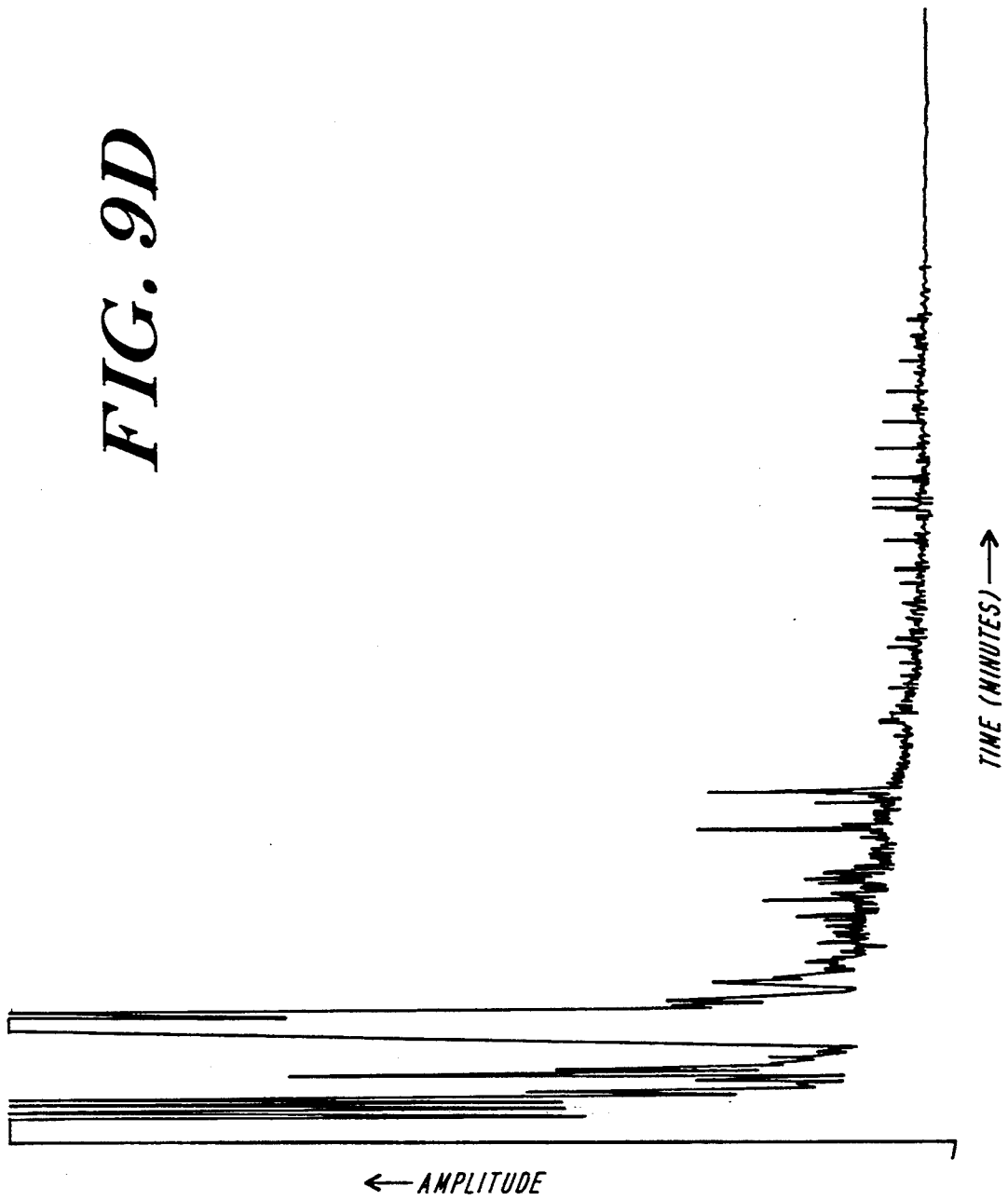

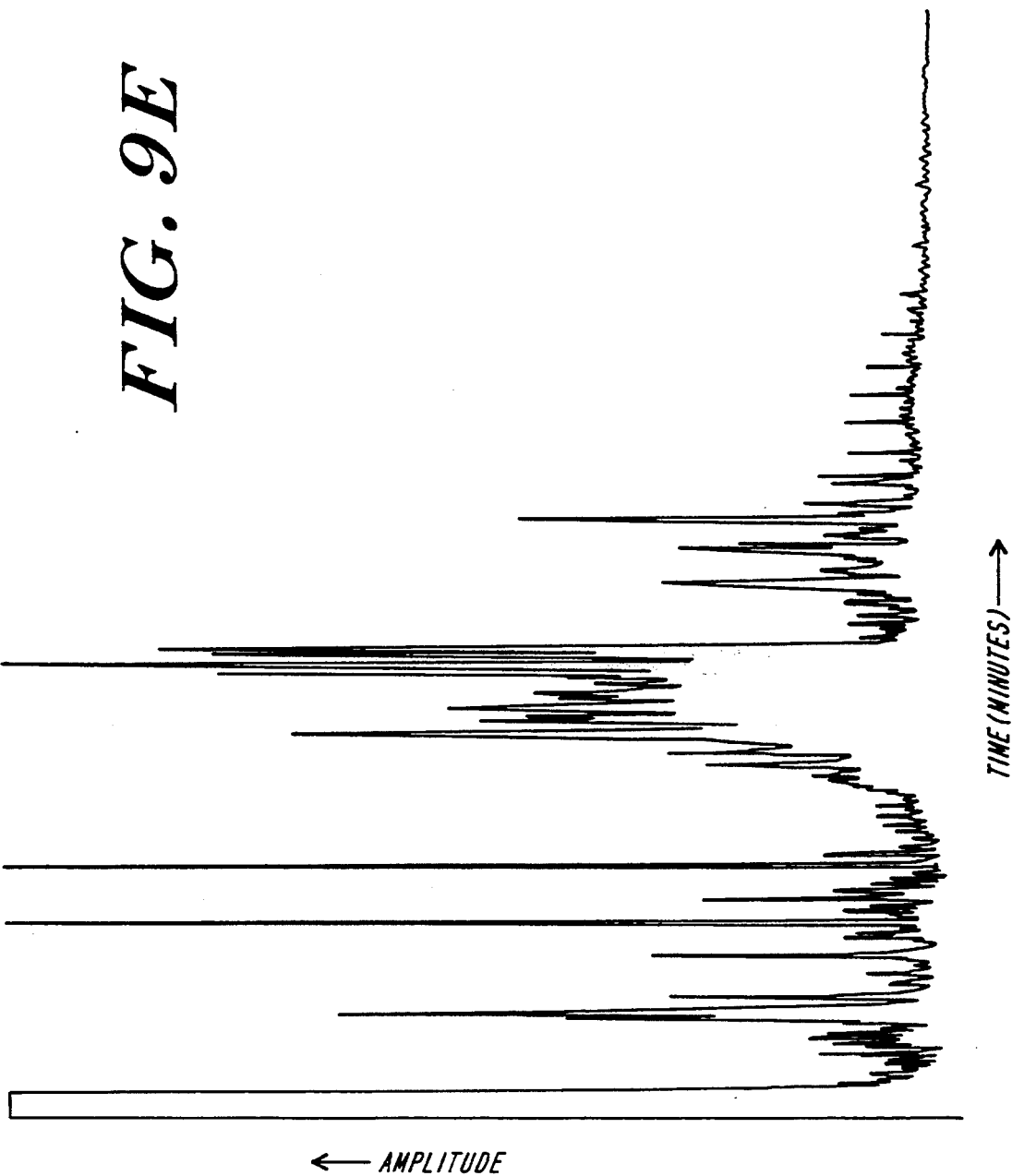

EXTRACTIVE HYDROGENATION FOR CHEMICAL ANALYSES

GOVERNMENT RIGHTS

Part of the work leading to this invention was made with United States Government funds. Therefore, the U.S. Government has certain rights in this invention.

FIELD OF THE INVENTION

The invention relates to processes for the chemical analysis of organic matter, particularly as trace compounds in a biological sample.

BACKGROUND OF THE INVENTION

Analysis of trace contaminants in biological samples (e.g., blood, urine, tissues, cell culture, plants and foods) and environmental samples (e.g., air, water and soil) is an important interest of government regulatory agencies, such as the U.S. Food and Drug Administration (FDA) and the Environmental Protection Agency (EPA). Existing analytical techniques employ a variety of detection strategies, emphasizing, e.g., high pressure/performance liquid chromatography (HPLC), gas chromatography (GC), mass spectrometry (MS) and capillary electrophoresis (CE).

A general limitation of existing methods is that a diversity of procedures is required to determine a wide variety of contaminants. For example, while mass spectrometry is a very powerful analytical technique, some forms of mass spectrometry are expensive, analyte-dependent, prone to down-time, or subject to contamination. Novel MS techniques such as electrospray (ES) have emerged, but the principle application of ES-MS has been to purified proteins. Impure small molecules are quite a different challenge, especially at trace levels. Particle beam mass spectrometry is not good for polar, thermally labile compounds. Immunoassays are limited by the requirement for specific antibodies, and are susceptible to interferences.. Capillary electrophoresis is not sufficiently sensitive for some analytes because of the small injection volumes. Also quite different conditions are generally necessary for different analytes.

Imaging analysis of biological and environmental samples is also important. In this technique, at least several of the constituents, usually major ones, of the sample are detected, as by chromatography, electrophoresis or mass spectrometry. This includes methods such as amino acid analysis in which a protein is hydrolyzed into its constituent amino acids, and the latter are detected.

SUMMARY OF THE INVENTION

Described herein is a new, general purpose technique called extractive hydrogenation analysis, useful for both trace component and imaging analysis of samples containing organic matter. In processes according to the invention, organic matter is thoroughly decomposed in the presence of a hydrogenation catalyst under substantially aqueous conditions into products, and one or more of the products is then detected.

In one aspect, the invention features an analytical process in which organic matter in a substantially aqueous sample is decomposed in the presence of a hydrogenation catalyst into one or more products; the reaction mixture includes a solid material that adsorbs at least one of the decomposition products; and the adsorbed product is later extracted from the solid material separately from the bulk of the nonadsorbed products and analytically detected. The solid material is typically washed to remove nonadsorbed materials prior to the extraction of the adsorbed product. In another aspect of the invention, at least one of the products which is detected is inorganic.

The invention also features a process in which polymeric organic matter that is substantially biological is thoroughly decomposed under substantially aqueous conditions in the presence of a hydrogenation catalyst into products of lower molecular weight.

Thorough decomposition of organic matter means that polymeric, O- or N-linked organic matter (like proteins, nucleic acids and polysaccharides) is thoroughly broken down into monomeric species, and that the double bonds between carbon atoms in monomer organic matter are thoroughly broken down into single bonds.

Biological matter is that which is synthesized by living organisms or their components. Nucleic acids, proteins, some lipids and polysaccharides, and combinations of these, are important biological polymers. The biological matter may comprise biological cells and tissue. The processes of the invention preferably are performed at a high temperature and pressure, and in the presence of a solid adsorbent and a relatively large amount of a catalyst (which may be a single species). The substantially aqueous solvent of the reaction may contain an alcohol functioning as a hydrogen-donating cosolvent.

The reaction products can be detected by a number of methods. For example, the larger, nonpolar products can be trapped by a nonpolar adsorbent, from which they can be conveniently extracted later thermally or with an organic solvent for subsequent detection by, e.g., gas chromatography. Inorganic components of the sample that are present in the aqueous phase at the end of the reaction also can be conveniently detected, by, e.g., spectroscopy, perhaps after prior separation by chromatography or electrophoresis.

Extractive hydrogenation, as described herein, changes the matrix of biological and some environmental samples in a unique way. This is because the structural integrity of many biological and related polymeric molecules relies on double or weak single bonds among the constituent atoms. By extensively removing these bonds, the described hydrogenation reaction creates a characteristic mixture of products that is radically different from what was present in the starting sample. For example, proteins, nucleic acids and polysaccharides are decomposed by such hydrogenation into compounds possessing saturated hydrocarbon frameworks, plus, at least from DNA, inorganic products like phosphate. This, along with the use of aqueous conditions, a solid phase adsorbent, and a high amount of catalyst, is what facilitates the detection of some components of the sample. The typically complex, aqueous, even insoluble initial sample is decomposed by the hydrogenation reaction into a simple, two-component mixture consisting of a clear, aqueous solution and solid adsorbent plus catalyst. When a nonpolar adsorbent is employed, the larger, nonpolar products of the reaction are adsorbed on the surface of the adsorbent at the end of the reaction, making it easy to recover them by extraction for detection, typically after washing away the bulk of the nonadsorbed products.

This technique will have many applications. It can be used, for example, to determine amino acids, lipids, carbohydrates, coenzymes, metabolites, drugs and their metabolites, pesticides, polyaromatic hydrocarbons and other pollutants, detergents, and inorganic species like phosphate, halides and metal ions. These analytes may be present free or as a component of other molecular species in the initial sample, e.g., proteins are polymers of amino acids, and polyaromatic hydrocarbons can become attached to nucleic acids. Different kinds of organisms such as different bacteria can be distinguished, as can different kinds of cells such as normal and leukemic white blood cells. The general composition of a biological sample, e.g., relative amounts of protein and nucleic acid, can be determined. Some information about the identity and purity of a protein sample can be obtained, including its overall content of extrinsic groups such as phosphate, coenzymes and metals. Antibiotics and other drug residues can be determined in foods.

Extractive hydrogenation according to the method of the invention is a simple, single-step, rapid, low-cost technique requiring minimal labor and technical skill by the operator, thus making it very easy to automate. Other techniques for sample preparation tend to involve multiple steps, utilize more equipment and/or reagents, take more time, and require more labor.

It is especially advantageous that intensive hydrogenation breaks down biological macromolecules (nucleic acids, proteins and polysaccharides) into small molecules. Some of the problems in other methods of sample preparation are due to the presence of macromolecules. These macromolecules may contaminate the equipment used for sample preparation and detection. They may bind some of the analyte and thereby make it harder to recover and purify this analyte prior to detection. They may give rise to interfering signals in the detection step. Extra effort can be necessary in sample preparation, increasing the time and expense, to deal with these problems. By breaking down macromolecules into small molecules, intensive hydrogenation overcomes or reduces many of the matrix problems due to macromolecules.

The described hydrogenation broadens the usefulness of gas chromatography-mass spectrometry (GC-MS), a widely-used and powerful detection technique. Macromolecules and polar compounds, because of their nonvolatility, thermal lability, or both are not compatible with GC-MS. Intensive hydrogenation can make the target component susceptible to detection by GC-MS by converting it into a daughter product which is volatile and thermally stable.

Multiple forms of a given analyte can be encountered in a sample, which can complicate the analysis. These multiple forms sometimes can be converted into a single daughter product by hydrogenation, simplifying the analysis.

A final advantage of the described hydrogenation is that it can avoid the use of caustic, expensive, toxic or problematical reagents that are sometimes necessary in other procedures for sample preparation. For example, hydrogenation can avoid the use of strong acids and bases, oxidizing agents, toxic solvents like acetonitrile or benzene, detergents, expensive antibodies, and carcinogenic alkylating agents that are part of other sample preparation methods.

BRIEF DESCRIPTION OF THE DRAWINGS

Other features and advantages of the invention will be apparent from the following description of the preferred embodiments thereof and from the claims, taken in conjunction with the accompanying drawings in which:

FIGS. 3A–3D show gas chromatograms from the analysis of a blank reaction mixture, 5 mg DNA, DNA spiked with 1 mg adduct, and DNA spiked with 0.1 mg adduct, respectively, according to the method of the invention;

FIG. 7A shows a gas chromatogram from the analysis of hydrolyzed hemoglobin, FIGS. 7B and 7C show a gas chromatogram from the analysis of 4-aminobiphenyl.

FIGS. 9A–9F show gas chromatograms from the analysis of different biological samples, according to the method of the invention.

DESCRIPTION OF PREFERRED EMBODIMENTS OF THE INVENTION

The method of the invention preferably combines extractive hydrogenation with gas chromatography (GC) to analyze biological samples. In the preferred method, the sample is subjected to intense hydrogenation at elevated temperature and pressure under aqueous conditions in the presence of excess (in terms of mass) palladium/carbon catalyst. These conditions convert the sample into a clear, aqueous solution devoid of macromolecules, and products with a saturated hydrocarbon framework result, the larger of which adsorb onto the carbon of the catalyst. These larger, adsorbed products are separately recovered by extracting the washed catalyst with an organic solvent, or thermally, and then are detected by GC, preferably using instruments fitted with a flame ionization or mass spectrometry detector.

Detection of the following trace analytes was achieved using the preferred conditions: (a) an acetylaminofluorenedeoxyguanosine DNA adduct spiked into DNA; (b) novobiocin, an antibiotic, spiked into milk; and (c) 4-aminobiphenyl, a carcinogen, spiked into hemoglobin. The technique also gives different GC chromatograms for *E. coli* and *Enterococcus* bacteria, thus providing an easy way of distinguishing contamination by these different genera.

To prepare the catalyst, 10 ml of toluene was added to 500 mg of 10% Pd/C in a 20 ml glass vial, the vial was capped, and the mixture was heated near boiling on a hot plate for 5 minutes. The mixture was then divided into 2 test tubes, centrifuged at 1500 rpm for 5 min, and the supernatant was decanted. The pellets were rinsed twice with 10 ml of toluene and then dried under nitrogen.

Figure 1:
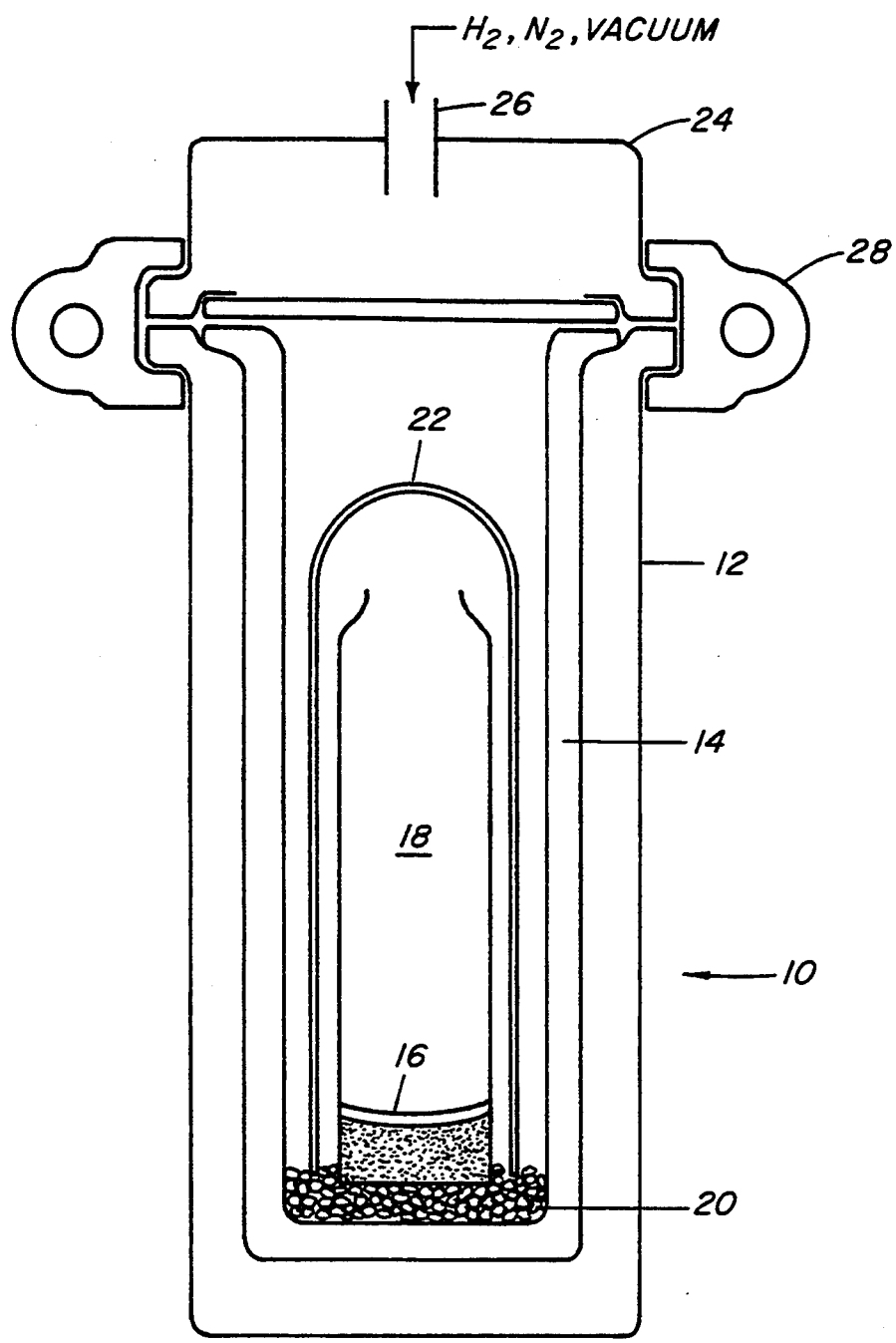
FIG. 1 shows apparatus for carrying out the method of the invention.

The hydrogenation apparatus consisted of a reactor and accompanying heater (High Pressure Autoclave, 75–150 ml, Berghof America, Concord, Calif., U.S.A.), and a manifold equivalent to that reported in Kresbach et al., (Anal. Chim. Acta 248:615–618 (1991)). Referring to FIG. 1, the reactor 10 consisting of a high temperature and pressure stainless steel vessel 12 was fitted with a PTFE-liner 14. In a typical reaction, an aliquot of an aqueous sample 16 was placed in a 20 ml glass vial 18 which, in turn, was loaded into the liner 14 on top of a layer of activated charcoal 20. A glass tube 22 was then inverted over vial 18. (The activated charcoal 20 and inverted tube 22 served to minimize contamination of the sample during the reaction.)

Reactor 10 was sealed with reactor cap 24 held by clamp 28, placed in an accompanying heater and connected to a manifold via stainless steel tubing for delivery of gases and application of a vacuum via inlet/outlet port 26. The heater was turned on, and after three cycles of vacuum/$N_2$ purging and three cycles of vacuum/$H_2$ purging, the $H_2$ pressure in the system was raised to 80 bar (1200 psi), according to the protocol described in Kresbach et al., supra. As the temperature was increased, the pressure in the reactor rose accordingly (up to 90 bar). During the reaction, the pressure decreased to about 70 bar (from consumption and leakage of $H_2$). At the end of the reaction the heater was shut off, and the reactor was allowed to cool for 2 h or more before being subjected to three cycles of vacuum/$N_2$. After the reactor was opened, the reaction vial was removed for reaction workup. The residual volume of the reaction mixture was generally about 1–2 ml when the vial intially contained 2–3 ml of water; the reaction mixture was dry after starting with 0.1–0.5 ml of water.

The reaction mixture was filtered through a 0.5 cm depth of "CELITE" (infuserial earth) in a scintered glass funnel (size 2 ml or 15 ml depending on the amount of catalyst), the "CELITE" (infusiorial earth) being pre-conditioned with 5 ml ethyl acetate, 5 ml of hot acetonitrile, and 5 ml of water, under vacuum suction, followed by 10 min of additional vacuum. Water (6 ml), used to rinse vial 18, was applied to the "CELITE" (infusorial earth) after the sample, and the vacuum was continued until the "CELITE" (infusorial earth), was dry. The filtrate was generally discarded, and the "CELITE" (infusorial earth) was eluted with 5 ml of ethyl acetate and 5 ml of hot acetonitrile. The combined organic phase was evaporated either on a rotary evaporator or under $N_2$ to a volume of about 1 ml, which was transferred to a tared vial prior to evaporation to dryness under $N_2$ and weighing. When the above reaction mixture was dry (from 0.1–0.5 ml of initial sample volume), it was transferred with ethyl acetate to the conditioned "CELITE" (infusorial earth) and eluted with ethyl acetate prior to the final evaporation and weighing steps.

The reaction residue generally was converted into a 1 $\mu g/\mu l$ solution in ethyl acetate, and 1 $\mu$ of solution was injected into a gas chromatograph for analysis. Initially a model 5890 Series II instrument fitted with a flame ionization detector (GC—FID) connected to a model 3392 Integrator (Hewlett Packard, Kennett Sq., Pa., U.S.A.) was used. The column was a fused silica capillary, OV (Ohio Valley) 5%, 30 meter column length, 0.25 mm ID, 0.25 $\mu$m film thickness (Ohio Valley, Marietta, Ohio, U.S.A.). Hydrogen (UHP) and air (Air Breathing Quality) were used for flame ionization detection, and helium (UHP) was used as the carrier gas. Conditions: injector, 140° C.; oven, 60° C. for injection then immediately up to 260° C. at 7° C. min for a 30 min hold; detector, 300° C.

Later GC-FID work was continued on a model 3740 gas chromatograph (Varian, Sugarland, Tex., U.S.A.) connected to a model 4270 Integrator (Spectra Physics, San Jose, Calif., U.S.A.). The column was a fused silica capillary, Ultra II, 25 m, 0.32 mm ID, 0.17 $\mu$m film thickness (Hewlett Packard). Gases used and reaction conditions were the same as described above, with the addition of nitrogen (UHP) as the detector make-up gas.

MATERIALS AND METHODS

Reagents

2-Aminofluorene, 2-nitrofluorene (98%), perhydrofluorene, 4-aminobiphenyl, dicyclohexyl, acetic anhydride, deoxyguanosine, 10% palladium on charcoal (10% Pd/C), and deuterated methanol for NMR were purchased from Aldrich (Milwaukee, Wis., U.S.A.). Ethyl alcohol U.S.P. (absolute 200 proof) was purchased from AAPER Alcohol and Chemical (Shelbyville, Ky., U.S.A.). 2-Propanol (HPLC grade), ethyl acetate (HPLC grade), hexane, triethylamine, ammonium hydroxide, potassium hydroxide, hydrochloric acid, pyridine, methanol (HPLC grade), acetonitrile (HPLC grade), "SOLUSORB" charcoal, dimethyl formamide (DMF), and "SPE" (solid phase extraction) C-18-cartridges were purchased from J. T. Baker (Phillipsburg, N.J., U.S.A.). DNA (type I, highly polymerized from calf thymus) was purchased from Sigma (St. Louis, Mo., U.S.A.). Salmon Sperm DNA was purchased from Calbiochem (San Diego, Calif., U.S.A.). Potassium sulfate (dibasic HPLC grade) was purchased from Fisher Scientific (Fair Lawn, N.J., U.S.A.). Sodium citrate (analytical reagent) was from Mallinckrodt (St. Louis, Mo., U.S.A.). Deuterated chloroform/1% TMS for NMR was from Cambridge Isotope Laboratories (Woburn, Mass., U.S.A.). The silicone oil (dimethyl silicone SF 96/50) was from Thomas Scientific (Swedesboro, N.J., U.S.A.). Filer papers #1 were purchased from Whatman (Hilsboro, Oreg., U.S.A.)."CELITE" (infusorial earth). Analytical Filter Aid was from Johns-Manville (Lompoc, Calif., U.S.A.). The bacteria (*E.* coli, and *Enterococcus*) were kindly provided as steady state samples in tryptic soy broth by Dr. Edward Schroder at Northeastern University, and were kept frozen until use. The deionized wetter was prepared using Barnstead NANOpure II/ORGANIC pure system. All gases were from Med-Tech (Medford, Mass.).

Additional Equipment

Mass spectrometry work was performed on a model 5890AGC gas chromatograph connected to a model 5971AMS mass selective detector (GC-MSD), with integration on a model VECTRA486S20 computer supplied with (part #) G1034B GC-MS operating software (Hewlett Packard). The column was a fused silica capillary HP-1, 12 m, 0.2 mm I.D., 0.33 μm film thickness (Hewlett Packard).

For high performance liquid chromatography an Econosil C8 Silica reversed-phase column, 250×4.6 mm, 10.0 μm particle size (Alltech, Deerfielld, Ill. U.S.A), was used. Detection was performed at 254 nm using a Spectromonitor III variable-wavelength detector (LDC-Milton Roy, Riviera Beach, Fl.), and integration was done using a model SP 4270 integrator.

Sample Preparation a) Milk

Skim milk (15 ml) or spiked skim milk (50 μl of 30 ng/μl novobiocin in isopropanol added to 15 ml of milk, followed by standing for 0.5 h) was applied to a ClS-silica solid phase extraction cartridge that had been preconditioned with 6 ml each of methanol and water using a slightly elevated pressure. The cartridge was washed with 6 ml each of water and methylene chloride, followed by elution with 6 ml each of acetonitrile/methanol, 50:50, v/v. The yellow solution was evaporated under nitrogen, giving 1 mg.

b) Bacteria i) *E. coli* in broth (stored frozen) was thawed and 7.5 ml were centrifuged at 5,000 RPM for 10 min at room temperature. The pellet was washed with 7.5 ml of water, and isolated as before by centrifugation.

ii) *Enterococcus* was prepared similarly, except 22.5 ml of thawed broth were taken initially to give a pellet the same size as that from *E. coli*.

c) Hemoglobin

A solution of 150 mg of hemoglobin or spiked hemoglobin in 100 ml of 6N HCl was refluxed for 24 hr. After neutralization with saturated sodium carbonate, an ethyl acetate extract (3×150 ml) was dried over sodium sulfate and rotary evaporated under vaccum. The residue was redissolved in 5 ml of ethyl acetate and re-evaporated under nitrogen in a vial, yielding 2 mg of solid. To this was added 50 mg of 10% Pd/C and 0.2 ml of water, followed by aqueous hydrogenation.

The following examples are presented to illustrate the advantages of the present invention and to assist one of ordinary skill in making and using the same. These examples are not intended in any way otherwise to limit the scope of the disclosure.

EXAMPLE I

Figure 2A:
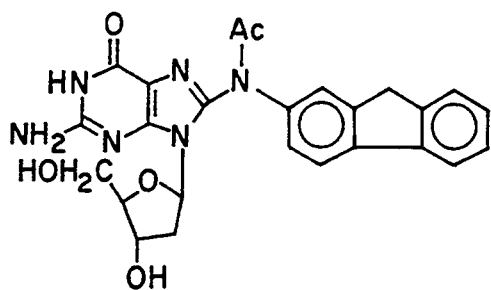
FIGS. 2A, 2B and 2C show typical sample adducts detectable by the method of the invention.
Figure 2B:
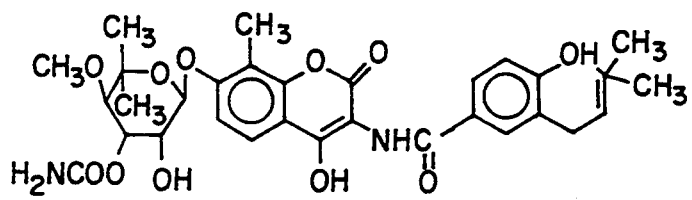
Figure 2C:
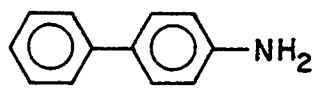
Figure 2D:
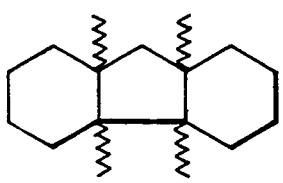
FIG. 2D, 2E and 2F show some of the products formed by the method of the invention; each depicted structure represents all of the possible stereoisomers of that structure.
Figure 2E:
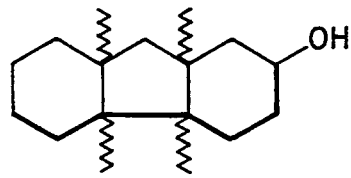
Figure 2F:
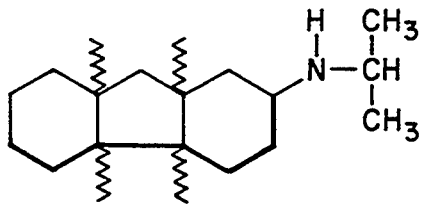
Figure 3C:
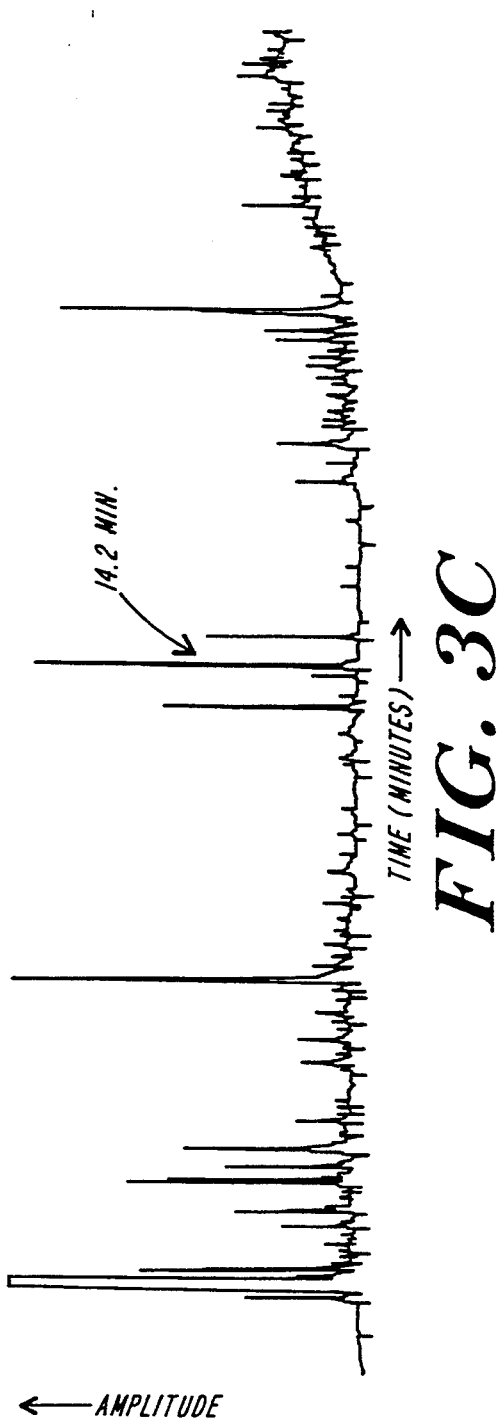
Figure 3D:
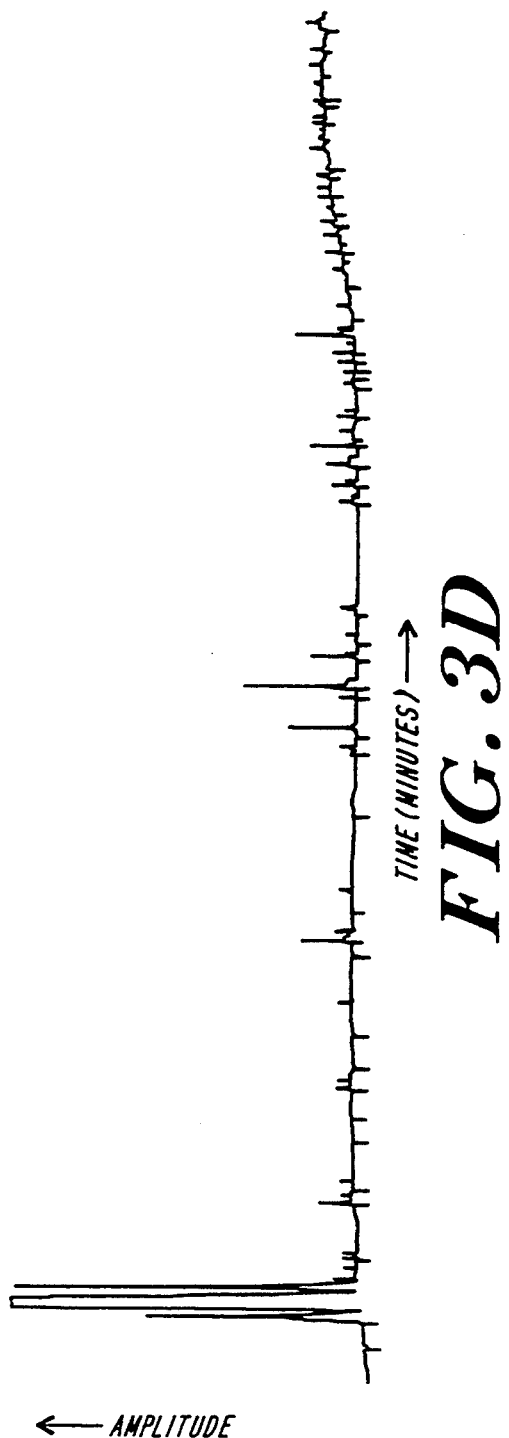

Extractive hydrogenation according to the method of the invention was performed on a sample of DNA in the presence and absence of N-acetoxy-N-acetyl-2-aminofluorene, a prominent DNA adduct shown in FIG. 2A. From a blank reaction consisting of 50 mg of 10% Pd/C catalyst in 2.5 ml of water, the GC-FID chromatogram shown in FIG. 3A was obtained. A corresponding sample containing 5 mg DNA gave the chromatogram shown in FIG. 3B. Spiking of 5 mg DNA sample with the compound of FIG. 2A 1 at levels of 1 mg and 0.1 mg gave the chromatograms shown in FIG. 3C and FIG. 3D, respectively, under reaction conditions of 150° C., $H_2$ pressure 60–80 bar, for 3 h. From a final volume of ethyl acetate solution of 50 μl, 1 μl was injected. The cluster of three peaks in the latter two chromatograms, with a retention time near 14 minutes, corresponds to the major products of compound mixture shown in FIG. 2D (based on GC-MS and co-injection of samples).

When the aqueous extract from hydrogenated DNA sample was evaporated, a white solid was obtained which was identified as sodium phosphate based on colorimetric analysis.

EXAMPLE II

Figure 4A:
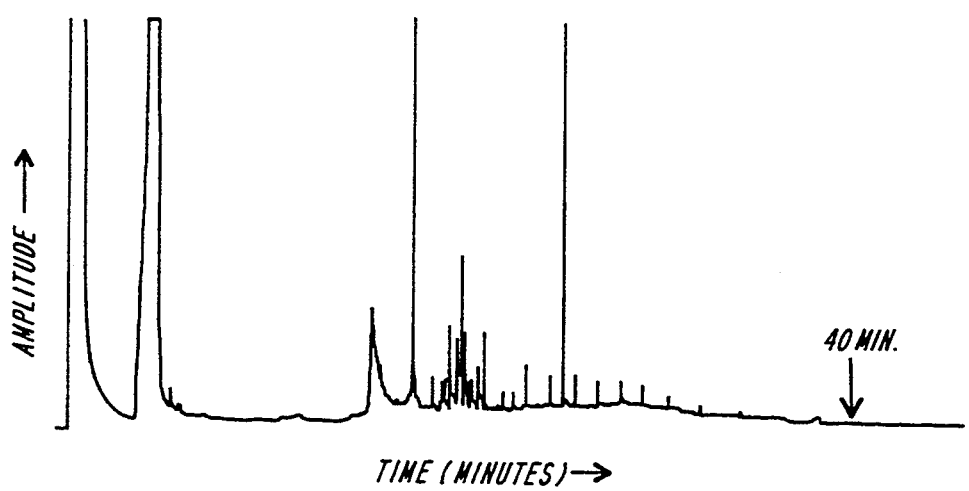
FIG. 4A shows a gas chromatogram from a blank reaction mixture.
Figure 4B:
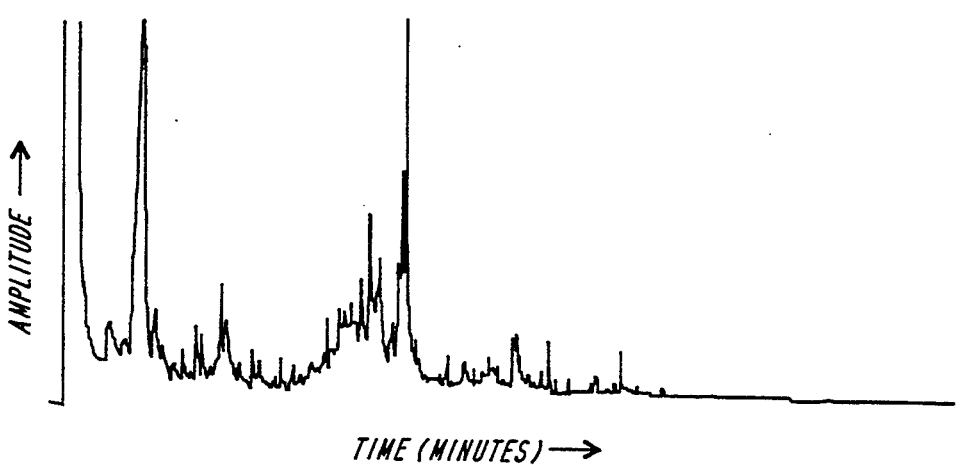
FIGS. 4B, 4C and 4D, 4E show duplicate gas chromatograms from the analysis of bacterial samples of E. coli and Enterococcus, respectively, according to the method of the invention.
Figure 4C:
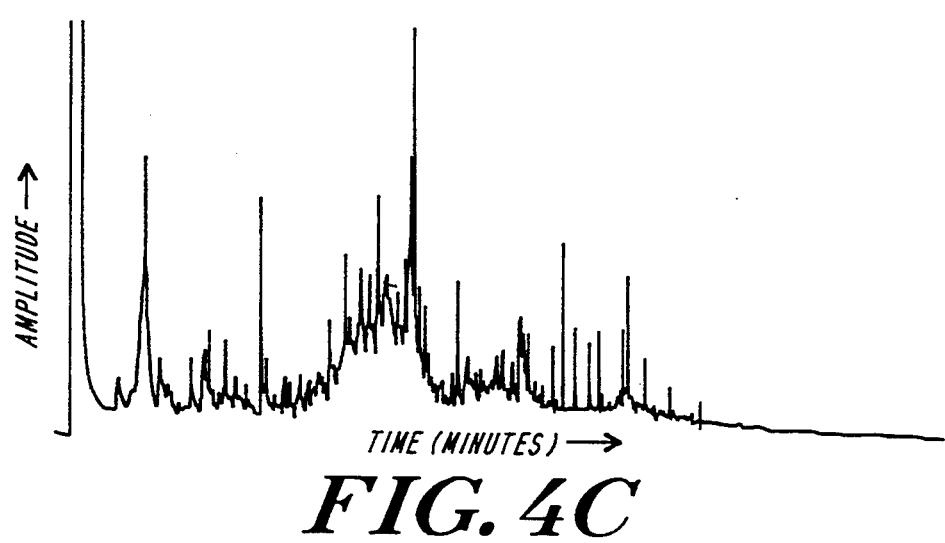
Figure 4D:
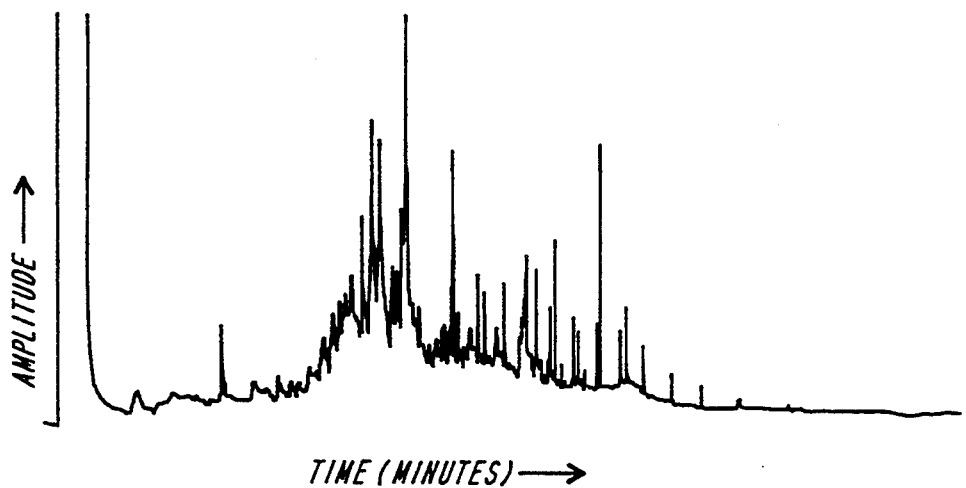
Figure 4E:
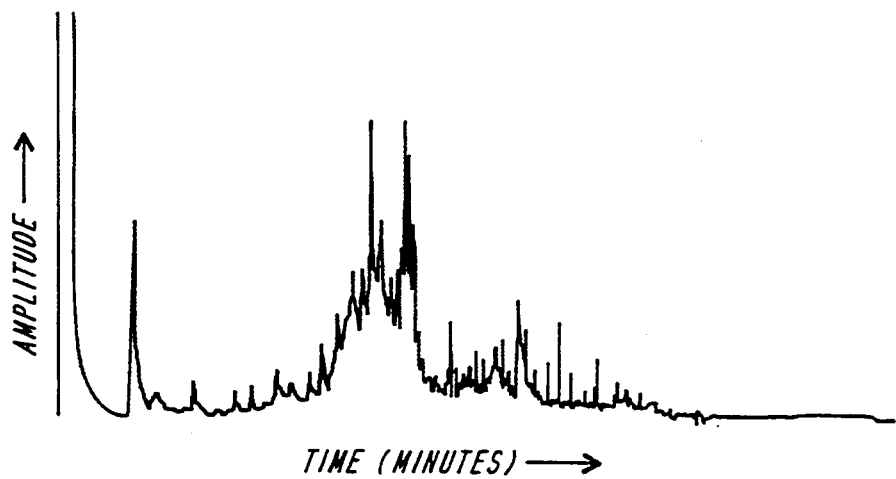

Hydrogenation of two bacterial samples, *E. coli* and *Enterococcus*, each in duplicate, led to GC-FID chromatograms shown in FIGS. 4B, 4C and 4D, 4E respectively, relative to that from a blank reaction, shown in FIG. 4A. The earlier retention range is richer in peaks for the chromatograms in FIGS. 4B and 4C vs those shown in FIGS. 4D and 4E, suggesting that the method of the invention can be used to distinguish different microorganisms.

EXAMPLE III

To show the potential for the method of the invention to be used to detect a drug which previously has fallen outside the range of GC, the antibiotic novobiocin, shown in FIG. 2A, was spiked into milk. An HPLC assay for novobiocin in milk was first performed in order to establish that the blank milk sample was truly devoid of the drug.

Figure 5A:
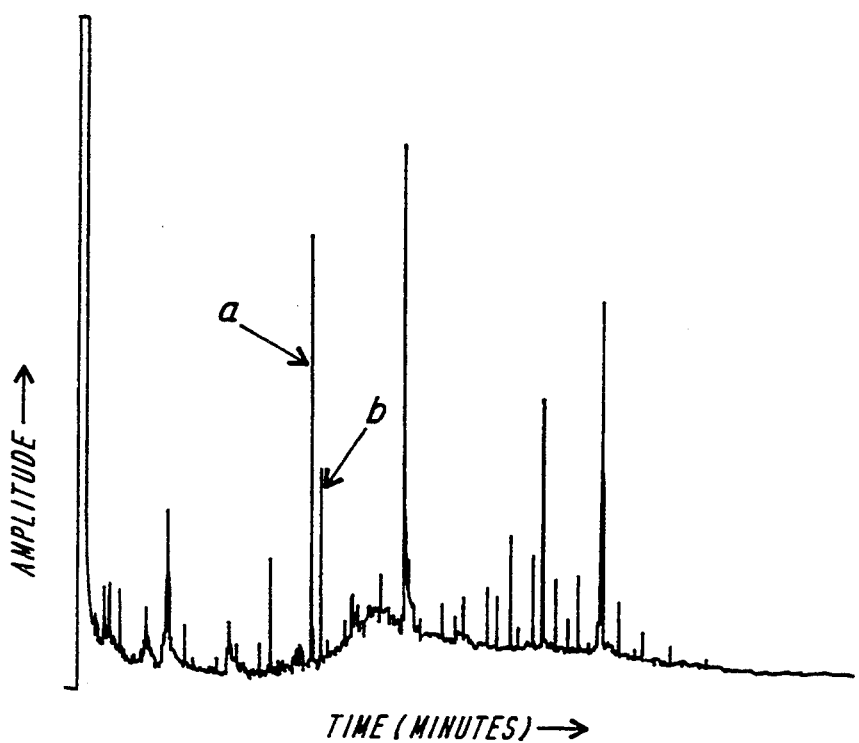
FIG. 5A shows a gas chromatogram from the hydrogenation of a standard of novobiocin.
Figure 5B:
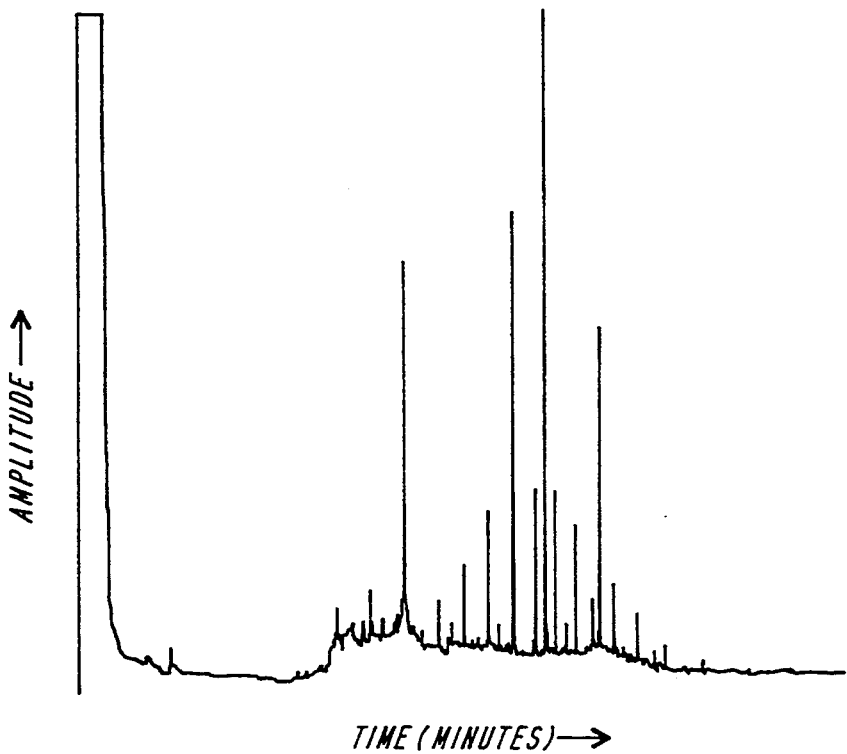
FIG. 5B shows a gas chromatogram of a blank reaction mixture.
Figure 5C:
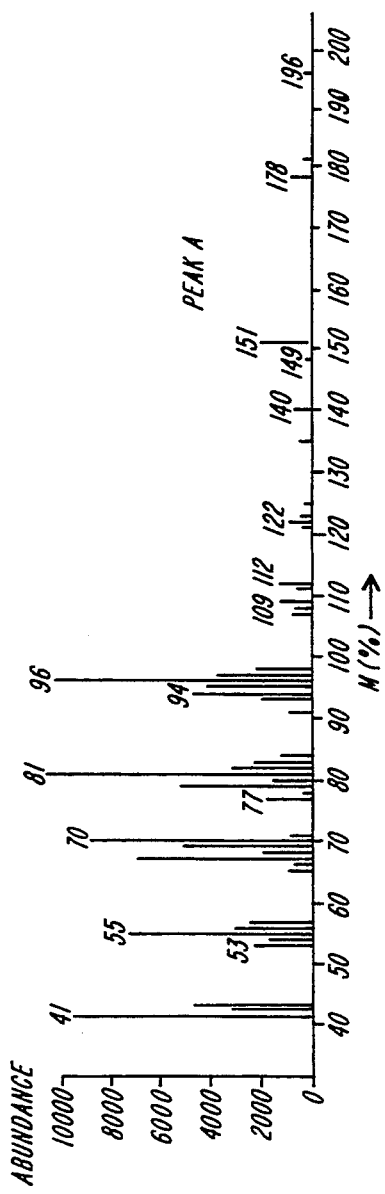
FIG. 5C show the mass spectrum of peak a of FIG. 5A.
Figure 5D:
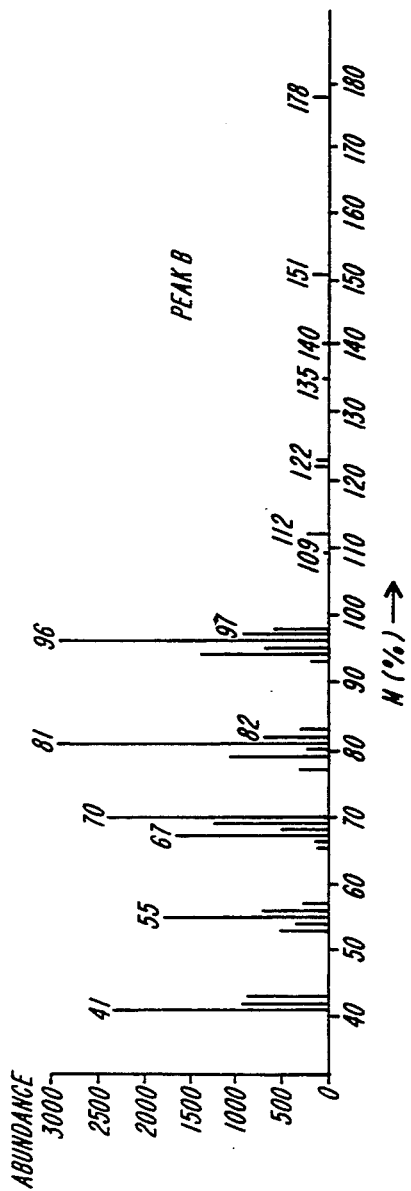
FIG. 5D shows the mass spectrum of peak b of FIG. 5A.

Hydrogenation of a standard of novobiocin (100 ng) followed by GC-FID gave the chromatogram shown in FIG. 5A. As seen, relative to a corresponding chromatogram from a blank reaction (FIG. 5B), two new peaks are observed. (Prior hydrogenation of a larger, standard sample of novobiocin had established that these two peaks derive from this compound.) The mass spectra of the two new peaks a and b are shown in FIGS. 5C and 5D, respectively.

Figure 6A:
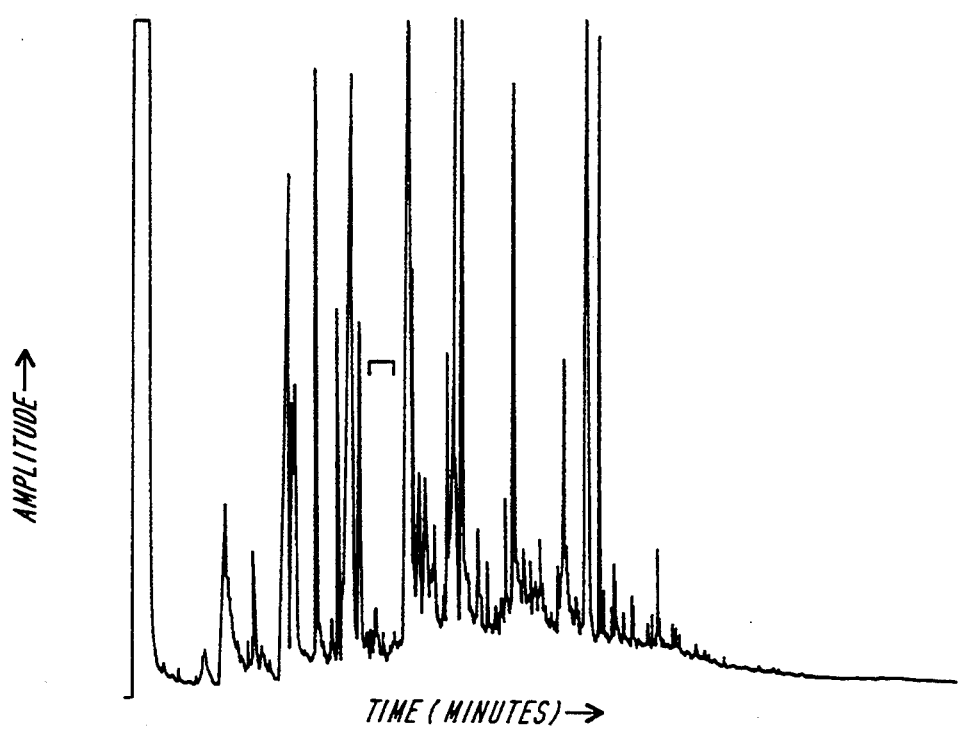
FIG. 6A shows a gas chromatogram from the analysis of milk without novobiocin, according to the method of the invention.
Figure 6B:
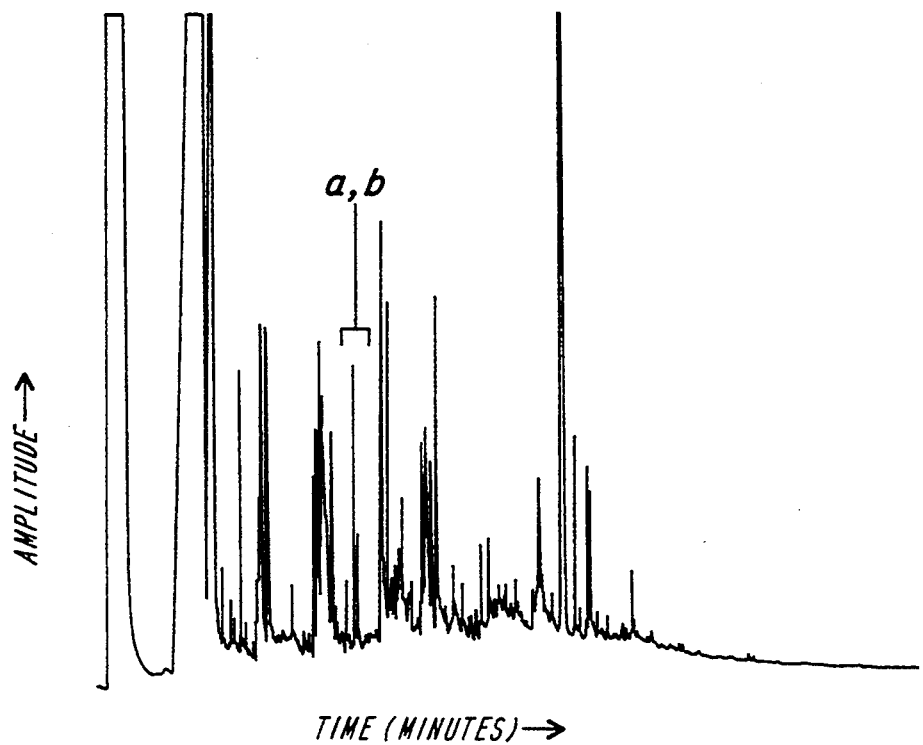
FIG. 6B shows a gas chromatogram from the analysis of milk with novobiocin, according to the method of the invention.

The detection by hydrogenation and GC-FID of 1.5 μg novobiocin spiked into milk is demonstrated in FIG. 6B relative to a blank chromatogram from unspiked milk, shown in FIG. 6A. As seen, the former chromatogram is distinguished by the pair of peaks (a, b) that was seen previously from standard novobiocin in FIG. 5A. Matching of this pair of peaks in the two chromatograms (FIGS. 5A and 6B) was established by co-injecting the samples.

EXAMPLE IV

Figure 7D:
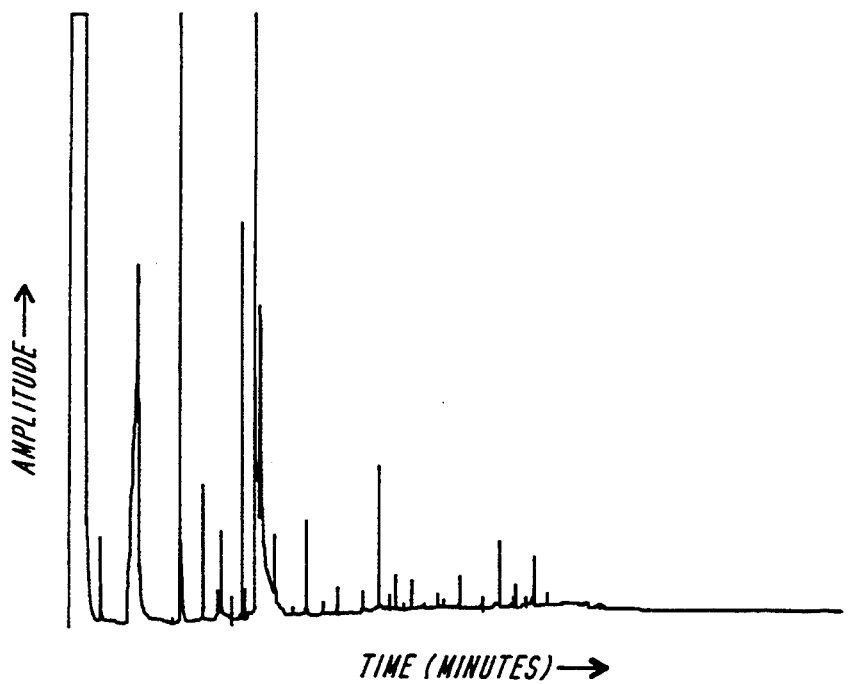
FIG. 7D shows a gas chromatogram from the analysis of hydrolyzed 4-amino-biphenyl.
Figure 7E:
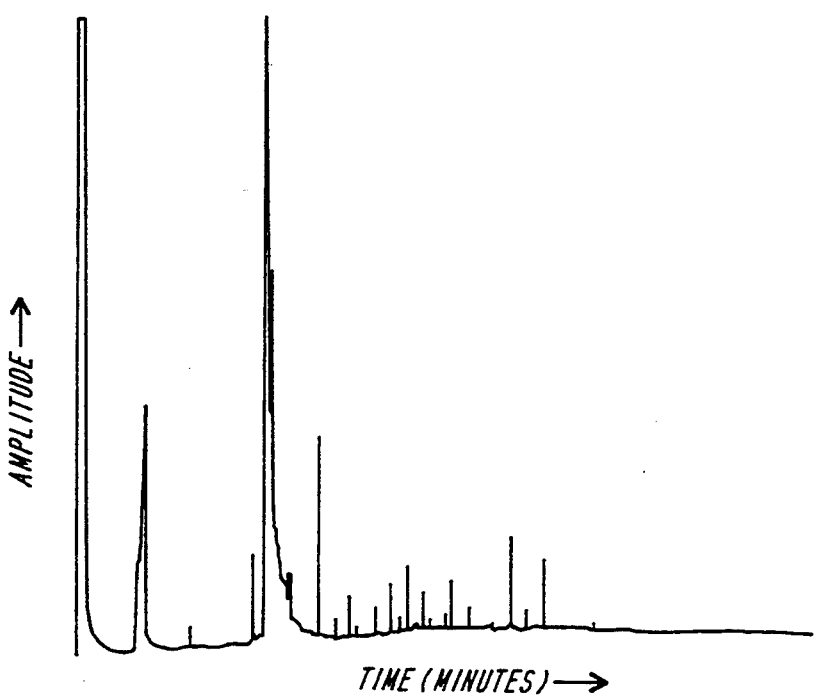
FIG. 7E shows a gas chromatogram from the analysis of hydrolyzed hemoglobin spiked with 4-aminobiphenyl prior to hydrolysis, all according to the method of the invention.
Figure 8:
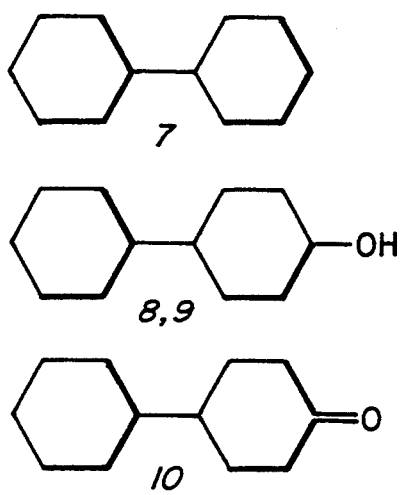
FIG. 8 shows products observed from the hydrogenation of 4-aminobiphenyl, according to the method of the invention.

Detecting metabolites of environmental carcinogens such as 4-aminobiphenyl bonded covalently to hemoglobin has been explored as a biomarker of human exposure to toxic chemicals (Bryant et al., Cancer Res. 47:602–608 (1987)). Therefore, the hydrogenation of 4-aminobiphenyl FIG. 2C, acid-hydrolyzed hemoglobin, and a mixture of these (including a control of "acid-hydrolyzed" 4-aminobiphenyl), led to the GC-FID and GC-MS chromatograms shown in FIGS. 7A–7D. FIG. 7A shows the GC-FID chromatogram from the hydrogenation of 150 mg of hydrolyzed hemoglobin in 200 μl of water. Referring to FIG. 7B, the hydrogenation of 4-aminobiphenyl yields four products that can be detected by GC-FID. These products were identified as known compounds by relying on the EI-MS library. Their structures are shown as compounds 7-10 in FIG. 8, and the inset to (FIG. 7C) shows the detection of compounds 8, 9 and 10 by GC-MS. FIG. 7D shows the hydrogenation of "hydrolyzed" 4-aminobiphenyl alone, and FIG. 7E demonstrates the detection of one mg of 4-aminobiphenyl spiked into 150 mg of hemoglobin.

EXAMPLE V

Figure 9F:
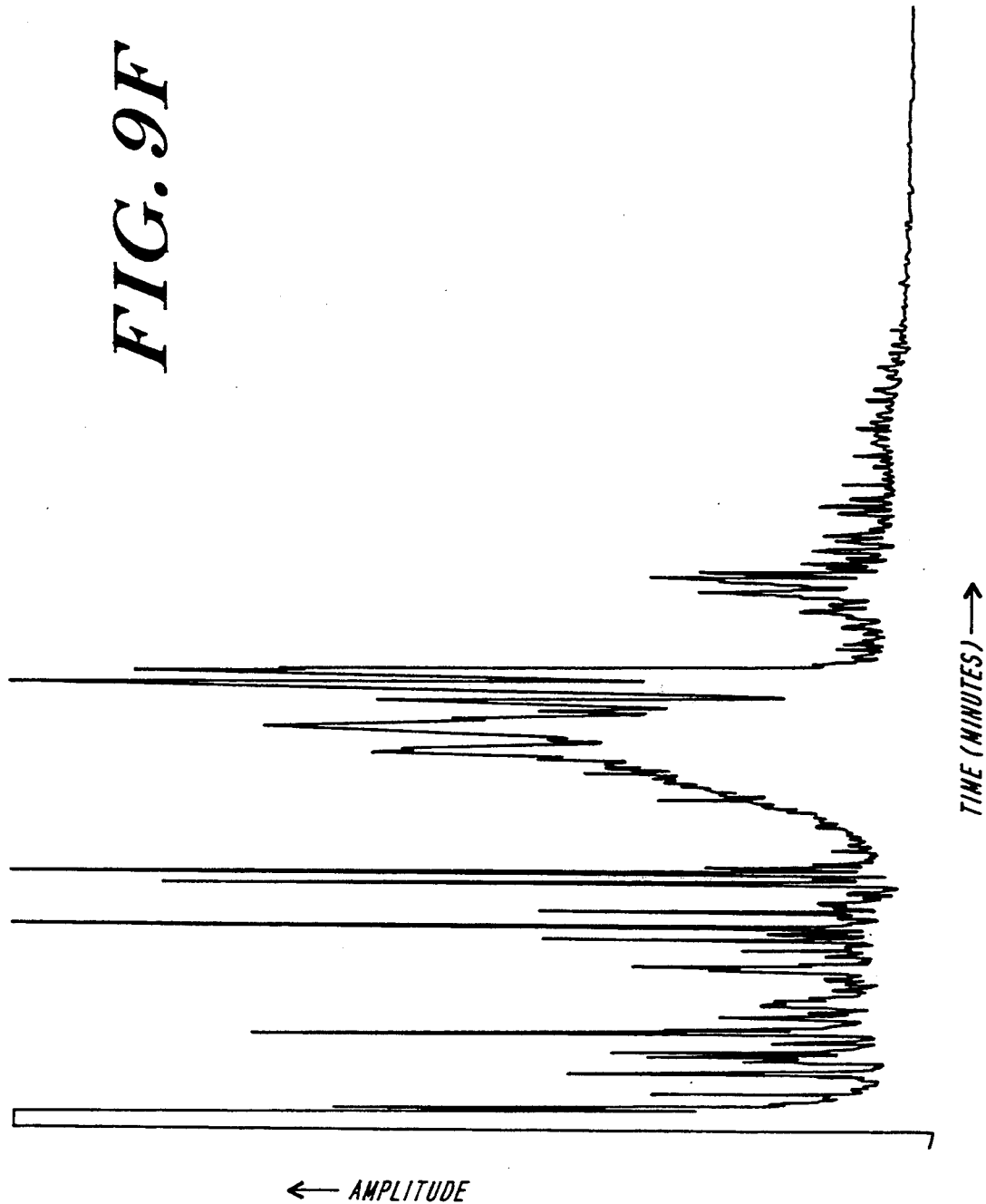

Quite different GC-FID chromatograms are obtained when a diversity of biological samples is subjected to hydrogenation and gas chromatography. Referring to FIGS. 9A-9F, GC-FID chromatograms are shown from the hydrogenation of: FIG. 9A—1 ml of milk spiked with 1 mg of novobiocin; FIG. 9B—50 mg of hemoglobin spiked with 1 mg of 4-aminobiphenyl; FIG. 9C—1.5 g of homogenized fish (using a Krieus-Lu (Switzerland) Kinematica CH-6010 homogenizer for 2 min); FIG. 9D—50 mg of corn starch; FIG. 9E—50 mg of bovine serum albumin; and FIG. 9F—50 mg of lysozyme. Each sample was dissolved in (or diluted to a volume of) 3 ml with water prior to the hydrogenation reaction. Hydrogenation conditions: 500 mg Pd/C, 150° C., 3 h, 60-80 bar. The final residues of 10.5, 7.4, 15.7, 7.4, 6.1, and 5.9 mg (A—F, respectively) were each dissolved in 1.0 ml of ethyl acetate (except 7.5 ml for C.), and 1 $\mu$l was injected.

Use

Ordinarily, conditions are selected for hydrogenation reactions that maximize the solubility of the reactants as well as products so that a high yield of the latter is obtained. This includes the selection of a catalyst that does not adsorb the desired products. Catalyst washings or elutions at the conclusion of the reaction are combined with the bulk reaction product.

In extractive hydrogenation, introduced here, a different strategy is adopted. A catalyst is selected, in this case palladium/carbon, along with water as the reaction solvent, so that the larger nonpolar products are hydrophobically extracted by the catalyst. The specific recovery of these adsorbed products, separate from the nonadsorbed products, leads to selectivity in what is recovered. In addition, hydrogenation to the point of thorough decomposition, without extraction, is attractive as a sample preparation technique for biological samples, since these samples are aqueous, and the proteins, nucleic acids and polysaccharides in the samples should be largely degraded to form volatile or polar, small molecules.

Irrespective of whether it is practiced in an extractive mode, intensive aqueous hydrogenation has interesting features as a sample preparation step for chemical analysis. In a simple way, it prepares a sample for analysis by gas chromatography, a widely used and powerful detection technique, especially in conjunction with mass spectrometry. The hydrogenation reaction is relatively nontoxic and safe, since water is the reaction solvent and only a small quantity of hydrogen is employed. In contrast to pyrolysis, a technique which tends to convert a biological sample into a char, hydrogenation as performed here converts the biosample into a clear solution. This hydrogenation technique should cause less random decomposition of sample than pyrolysis, giving hydrogenation more potential for trace component analysis.

Extractive hydrogenation can also be employed for additional analytical purposes. First, it can facilitate the detection of the total amount of inorganic species such as halide or phosphate salts in a sample. These species will be recovered in the aqueous phase at the end of the hydrogenation reaction. Second, the molecular fragmentation achieved by the method of the invention, assuming that the fragments can be identified by MS, would provide some clues about the structure of a known or unknown substance.

The apparatus used for the method of the invention could easily be adapted for automation. For example, each sample to be analyzed would be placed in an individual vial positioned on a conveyor belt. The vials would be transported into a heat room, individually capped with a fitted top equipped with an appropriate input/output port, and the sample would be subjected to extensive hydrogenation, as described. After the hydrogenation was complete, the cap would be removed from the vial, the sample would be taken to dryness, perhaps washed, extracted or both, and the vial would be moved to the gas chromatograph where the sample or extract would be thermolyzed directly for analysis.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A process for chemical analysis of organic matter comprising the steps of:
   providing an aqueous sample containing organic matter;
   thoroughly decomposing said aqueous sample in a hydrogenation reaction in the presence of a hydrogenation catalyst, which catalyst comprises palladium metal on a solid nonpolar adsorbent material into products, said products comprising polar products and nonpolar products, said solid nonpolar adsorbent material adsorbing at least one of said nonpolar products;
   recovering said solid nonpolar adsorbent material containing said at least one adsorbed nonpolar product;
   extracting said at least one adsorbed nonpolar product from said nonpolar solid adsorbent material;
   recovering said at least one adsorbed nonpolar product separately from the bulk of the nonadsorbed products; and
   detecting said at least one adsorbed nonpolar product.

2. The analytical process of claim 1 wherein said organic matter is substantially biological.

3. The analytical process of claim 1 wherein said organic matter is substantially biological and polymeric.

4. The analytical process of claim 1 wherein said organic matter is substantially biological cells or tissue.

5. The analytical process of claim 1 wherein said organic matter is substantially protein, nucleic acid, polysaccharide, or a mixture of these.

6. The analytical process of claim 1 wherein said organic matter is substantially lipid.

7. The analytical process of claim 1 wherein, in said decomposing step, the weight of said catalyst is greater than the weight of said organic matter.

8. The analytical process of claim 1 wherein, in said decomposing step, the weight of said catalyst is greater than five times the weight of said organic matter.

9. The analytical process of claim 1 wherein, in said decomposing step, the weight of said catalyst is greater than twenty times the weight of said organic matter.

10. The analytical process of claim 1 wherein said sample is allowed to go to dryness during said decomposing step.

11. The analytical process of claim 1 wherein in said decomposing step, said hydrogenation reaction is performed in a substantially hydrogen atmosphere.

12. The analytical process of claim 1 wherein, in said decomposing step, said hydrogenation reaction is performed in the presence of a hydrogen-donating co-solvent.

13. The analytical process of claim 1 wherein said decomposing step is performed in a reaction chamber in a substantially hydrogen atmosphere and wherein the temperature in said reaction chamber during said hydrogenation reaction is greater than 50° C. and the hydrogen pressure in said reaction chamber during said hydrogenation reaction is greater than 100 psi.

14. The analytical process of claim 13 wherein the hydrogen pressure in said reaction chamber during said hydrogenation reaction is greater than 500 psi.

15. The analytical process of claim 1 wherein, in said decomposing step, said catalyst further comprises a carbon matrix.

16. The analytical process of claim 1 wherein, in said decomposing step, said hydrogenation catalyst comprises said solid adsorbent material.

17. The analytical process of claim 1 wherein, in said extracting step, said adsorbed products are extracted with an organic solvent.

18. The analytical process of claim 1 wherein said at least one product extracted from said solid adsorbent material and detected possesses a saturated hydrocarbon framework.

19. The analytical process of claim 1 wherein said at least one product extracted from said solid adsorbent material and detected is a saturated hydrocarbon.

20. The analytical process of claim 1 wherein said at least one product extracted from said solid adsorbent material and detected is a saturated hydrocarbon alcohol.

21. The analytical process of claim 1 wherein said at least one product extracted from said solid adsorbent material and detected is a saturated hydrocarbon ketone.

22. The analytical process of claim 1 wherein said detecting step comprises chromatography or electrophoresis.

23. The analytical process of claim 22 wherein said detecting step further comprises mass spectrometry.

24. The analytical process of claim 22 wherein said detecting step takes place in the gas phase.

25. The analytical process of claim 1 wherein said at least one product detected in said detecting step is derived from a drug contaminant of said organic matter.

26. The analytical process of claim 1 wherein said at least one product detected in said detecting step is derived from an environmental pollutant or food additive contaminant of said organic matter.

* * * * *

UNITED STATES PATENT AND TRADEMARK OFFICE
CERTIFICATE OF CORRECTION

PATENT NO. : 5,445,966
DATED : August 29, 1995
INVENTOR(S) : Roger W. Giese, et al.

It is certified that error appears in the above-indentified patent and that said Letters Patent is hereby corrected as shown below:

```
Column 5, line 60, "(infuserial earth)" should read
--(infusorial earth)--.

Column 5, line 62, "(infusiorial earth)" should read
--(infusorial earth)--.

Column 6, line 14, "1 µof" should read --1µ of--.

Column 6, line 65, "Filer papers" should read
--Filter papers--.

Column 7, line 4, "wetter" should read --water--.

Column 7, line 29, "CIS-" should read -- C18- --.

Column 8, line 4, "FIG. 2A 1 at" should read --FIG. 2A at--.

Column 8, line 11, "of compound" should read --of the
compound--.
```

Signed and Sealed this

Thirteenth Day of August, 1996

Attest:

BRUCE LEHMAN

*Attesting Officer*      *Commissioner of Patents and Trademarks*